US005831069A

United States Patent [19]
Barik

[11] Patent Number: 5,831,069
[45] Date of Patent: Nov. 3, 1998

[54] ANTISENSE OLIGONUCLEOTIDES AGAINST NONSTRUCTURAL PROTEINS NS1 AND NS2 OF RESPIRATORY SYNCYTIAL VIRUS AND USES THEREOF

[75] Inventor: Sailen Barik, Mobile, Ala.

[73] Assignee: South Alabama Medical Science Foundation, Mobile, Ala.

[21] Appl. No.: 811,322

[22] Filed: Mar. 4, 1997

[51] Int. Cl.$^6$ .......................... C07H 21/02; C07H 21/04; C12Q 1/68
[52] U.S. Cl. .......................... 536/24.5; 435/6; 435/172.1; 435/375; 536/23.1; 536/24.1; 536/24.3; 514/44
[58] Field of Search .......................... 435/6, 172.1, 375; 536/23.1, 24.1, 24.5, 24.3; 514/44

[56] References Cited

FOREIGN PATENT DOCUMENTS 9522553  8/1995  WIPO .

OTHER PUBLICATIONS

Branch, A. A Good Antisense is Hard to Find. TIBS vol. 23 :45–50, Feb. 1998.

Jairath, S., et al. Inhibition of Respiratory Syncytial Replication by Antisense Oligodeoxyribonucleotides. Antiviral Research vol. 33:201–213, Feb. 1997.

Primary Examiner—John L. LeGuyader
Assistant Examiner—Sean McGarry
Attorney, Agent, or Firm—Benjamin Aaron Adler

[57] ABSTRACT

The present invention provides an oligonucleotide having the nucleotide sequence complementary to the respiratory synctial virus nucleotide sequencenumber 98-116 of the respiratory synctial virus antigenome or nucleotide sequence number 627-645 of the respiratory synctial virus antigenome. Also provided is a composition comprising an oligonucleotide according the present invention and a physiologically acceptable carrier therefore. Also provided are various methods of using these novel oligonucleotides.

6 Claims, 10 Drawing Sheets

ANTISENSE OLIGONUCLEOTIDES AGAINST NONSTRUCTURAL PROTEINS NS1 AND NS2 OF RESPIRATORY SYNCYTIAL VIRUS AND USES THEREOF

BACKGROUND OF THE INVENTION

1. Field of the Invention

The present invention relates generally to the fields of molecular virology and pharmacology. More specifically, the present invention relates to antisense oligonucleotides against nonstructural proteins NS1 and NS2 of respiratory syncytial virus and uses thereof.

2. Description of the Related Art

Human respiratory syncytial virus (RSV), a member of the genus Pneumovirus in the family Paramyxoviridae, is the single most important infectious agent of pediatric respiratory disease (Heilman, 1990; Hall, 1994). A recurring cause of pneumonia-like diseases that include "croup" in young children, respiratory syncytial virus accounts for significant morbidity in the first years of the human life, claiming nearly 4 million human lives worldwide. In the United States, respiratory syncytial virus produces about 60,000 hospitalizations per year, resulting in nearly 25,000 deaths. The nonsegmented negative-stranded genomic RNA (vRNA) of human respiratory syncytial virus is 15,222 nucleotides long. Nucleotide sequence analysis and cloning of the viral genes have resulted in the identification of ten major protein coding sequences as well as putative regulatory sites, i.e., the intergenic regions and the genome termini ("leader" and "trailer" sequences). This has led to the establishment of the following gene order: 3'-(leader)-NS1-NS2-N-P-M-SH-G-F-22K-L-(trailer)-5' (reviewed by Collins, 1991).

Unique genetic features of respiratory syncytial virus differentiate it from other paramyxoviruses (Collins, 1991). Notable among them is the presence of extra genes, viz., SH (or 1A), NS1 (NS1), NS2 (NS2), and M2 (or 22K). NS1 and NS2 appeared interesting for the following reasons. First, while the homolog of the respiratory syncytial virus SH and M2 genes are found in a few other paramyxoviruses, gene sequences homologous to NS1, NS2 have not been found in any organism. Second, while the nucleocapsid protein gene N is the most 3'-terminal gene in the genomes of all nonsegmented negative-strand RNA viruses, in pneumoviral genomes such as that of respiratory syncytial virus, NS1 and NS2 genes precede N (see gene order above). Third, NS1 and NS2 mRNAs are among the most abundant viral gene transcripts synthesized in vivo as well as in vitro (Barik, 1992), which is in accord with the polarity of transcription observed in nonsegmented negative-strand RNA viruses in general. The corresponding proteins are also found in relatively large amounts in RSV-infected cells. In contrast, these proteins cannot be detected in mature RS virions and are therefore, considered nonstructural in nature (hence their alternate names, NS1 and NS2, respectively).

However, the function(s) of these two abundant yet nonstructural proteins remain completely unknown. Both NS1 and NS2 proteins are small, their calculated molecular weights based on nucleotide sequences of the genes being 15.5 kD (NS1) and 14.5 kD (NS2) (Collins and Wertz, 1985; Elango et al., 1985; Huang et al., 1985). NS2 polypeptide is slightly basic overall, while NS1 is neutral in charge. Except for these information, the primary sequences of these proteins do not provide any clue regarding their function. It is not known whether the genes are essential for virus growth. In the absence of viral mutants mapping in these genes, the corresponding mutational phenotypes also remain unknown.

The prior art is deficient in the lack of effective means of inhibiting the transmission and replication of the human respiratory syncytial virus. The present invention fulfills this longstanding need and desire in the art.

SUMMARY OF THE INVENTION

The nonstructural protein genes 1C (NS1) and 1B (NS2) of human respiratory syncytial virus (Long strain) were cloned and sequenced. The recombinant proteins were expressed in bacterial and baculovirus expression systems as well as translated in wheat germ lysates in vitro, and antibodies were generated against recombinant proteins. Phenotypic mutants of nonstructural (NS) proteins NS1 (NS1) and NS2 (NS2) of respiratory syncytial virus (RSV) were created by the use of specific antisense deoxyoligonucleotides spanning the translation initiation region of the corresponding mRNAs. In vitro as well as ex vivo, the oligonucleotides caused a near-complete inhibition of NS1 and NS2 protein synthesis. Inhibition of synthesis of either or both proteins within the first few hours of infection led to a drastic reduction in viral titer and syncytia in cultured cells. However, there was no appreciable effect on viral transcription, replication, or translation of individual viral proteins. Neither oligonuclotide produced any detectable cytopathic effect. Immunological studies using specific antibodies revealed that both proteins were abundant in the cytoplasm of infected cells. Both proteins could be detected as early as 2 hours post-infection, reached maximal levels at 16–20 hours, and gradually decreased at later times. Consistent with their nonstructural nature, neither protein was detectable in the mature virions. The half-lives of NS1 and NS2 in infected cells were 1 hour and 20 minutes, respectively. In vitro, recombinant soluble NS proteins expressed in a baculovirus system showed a moderate affinity for binding to viral nucleocapsids. It appears that the two NS proteins function together and are essential in a post-replicative stage of virus growth, making them targets for antiviral therapy.

In one embodiment of the present invention, there is provided an oligonucleotide having the nucleotide sequence complementary to the respiratory synctial virus nucleotide sequence number 98-116 of the respiratory synctial virus antigenome or nucleotide sequence number 627-645 of the respiratory synctial virus antigenome.

In another embodiment of the present invention, there is provided a oligonucleotide according to the present invention and a physiologically acceptable carrier therefore.

In yet another embodiment of the present invention, there is provided an oligonucleotide having the nucleotide sequence: CAATGAATTGCTGCCCATC (SEQ ID No. 1).

In still yet another embodiment of the present invention, there is provided an oligonucleotide having the nucleotide sequence: TTGTGGGTTGTGTCCATG (SEQ ID No. 2).

In still yet another embodiment of the present invention, there is provided a method of killing respiratory synctial virus in an individual in need of such treatment, comprising the step of contacting said virus with an effective dose of the oligonucleotide of the present invention.

In still yet another embodiment of the present invention, there is provided a method of treating respiratory synctial virus syndrome in an individual in need of such treatment, comprising the step of administering to said individual an effective dose of the oligonucleotide of the present invention.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows the expression of recombinant NS proteins in bacteria. E. coli BL21(DE3) cells transformed with pET-3a-NS1 (panel A) or pET-3a-NS2 (panel B) clone were grown in LB containing ampicillin (100 µg/ml) and glucose (20 mM) and induced with IPTG (0.5 mM) exactly as described (Mazumder et al., 1994). Lysis of the cells, isolation of the membrane fraction, and its solubilization by guanidinium hydrochloride (Gn-HCl) were also carried out essentially as described (Mazumder et al., 1994). The various fractions (~5–20 µg protein) were analyzed in SDS-PAGE (20% total acrylamide; acrylamide: bisacrylamide= 30:0.4) according to Laemmli (1970); the coomassie blue-stained protein pattern is shown. For both panels A and B: Lanes 1 and 2: total protein of uninduced and induced cells, respectively; lane 3: S100 extract; lane 4: Gn-HCl-insoluble fraction of the membrane. For panel A: lane 5: fraction corresponding to lane 7 obtained from BL21(DE3) cells containing just pET-3a vector; lanes 6 and 7: soluble and insoluble fraction, respectively, after removal of Gn-HCl by dialysis. For panel B: lane 5: insoluble NS1 protein fraction following removal of Gn-HCl by dialysis. M=standard protein markers, numbers indicating MW values in kD. Arrows point to the NS2 (~17 kD) and NS1 (~13 kD) bands FIG. 2 shows the translation of NS proteins in vitro. The following templates were transcribed in vitro with T7 RNA polymerase and the resulting mRNAs were translated in wheat germ extracts in the presence of $^{35}$S-methionine: pGEM-4-NS2, linearized with EcoRI (lane 1) or NheI (lane 2); pET-3a-NS2 linearized with BamHI (lane 3); and pET-3a-NS1 linearized with BamHI (lane 6). The proteins were analyzed by SDS-PAGE as described for FIG. 1; an autoradiograph of relevant lanes (0, 1, 2, 3, and 6) is shown along with stained lanes (4, M, and 5). Lane 0 represents a translation reaction without any mRNA added. Lanes 4 and 5 represent purified bacterial NS2 and NS1, respectively; lane M shows standard protein markers as in FIG. 1. NS2 and NS 1 bands are indicated with arrows.

FIG. 3 shows the expression of soluble NS proteins in insect cells. Both genes were cloned into the EcoRI and BglII sites of pVL1392 (Pharmingen, San Diego, Calif.) and recombinant baculoviruses were obtained by co-transfection with BaculoGold DNA. Sf21 cells were infected by the recombinant viruses and at 4 days p.i., cells were collected and lysed by sonication. To purify NS2/1B (lanes 1–3) and NS1/1C (lanes 1–4) proteins, S100 extracts made from the total lysates were chromatographed through Sephadex G-25 and the fractions containing the recombinant proteins were detected by SDS-PAGE and pooled. About 10 mg of the following fractions were analyzed on SDS-PAGE; a coomassie-blue stained gel is shown. 1,4=total extract; 2,5= S100; 3,6=purified proteins.

FIG. 4 shows the intracellular localization of NS1 (1C) and NS2 (1B). HEp-2 monolayers, infected with respiratory syncytial virus at an m.o.i. of 2.0 ('A' and 'B'; or uninfected controls, 'a' and 'b') were fixed with methanol-acetone at 30 h p.i., probed with anti-1B ('A' and 'a') or anti-1C ('B' and 'b') antibodies, and finally with FITC-conjugated anti-rabbit IgG essentially as described (Dean et al., 1995).

FIG. 6 shows the immunoblot detection of intracellular NS (1B/1C) proteins. Western blot analysis was carried out using a mixture of anti-NS1 or anti-NS2 antibodies as described below. Lanes 0=uninfected; 1=oligo-untreated; 2=AS2-treated; 3=AS1-treated.

Lanes 0=uninfected; 1=untreated (no oligo); 3=AS2-treated; 4=AS1-treated. The various respiratory syncytial virus protein bands are indicated.

DETAILED DESCRIPTION OF THE INVENTION

In the present invention, the generation of cloning and sequencing of the NS genes of the respiratory syncytial virus (Long) and generation of recombinant NS proteins and specific anti-NS antibodies is described. Using these reagents, the intracellular location and stability of NS proteins and their interaction with viral nucleocapsids was examined. In another approach, synthetic oligonucleotides (abbreviated as "oligo"s) antisense to the NS1 and NS2 mRNAs were used to generate phenotypic mutants of these proteins. The present invention provides the first evidence for a direct role of the nonstructural proteins in respiratory syncytial virus growth, most likely in a post-replicative step.

The present invention is directed to an oligonucleotide having the nucleotide sequence complementary to the respiratory synctial virus nucleotide sequence number 98-116 of the respiratory synctial virus antigenome or nucleotide sequence number 627-645 of the respiratory synctial virus antigenome. The present invention is also directed to a composition comprising an oligonucleotide according the present invention and a physiologically acceptable carrier therefore. Preferably, an oligonucleotide of the present invention has the nucleotide sequence: CAATGAATTGCT- GCCCATC (SEQ ID No. 1) or the nucleotide sequence: TTGTGGGTTGTGTCCATG (SEQ ID No. 2).

The present invention is also directed to a method of killing respiratory synctial virus in an individual in need of such treatment, comprising the step of contacting said virus with an effective dose of the oligonucleotide of the present invention.

The present invention is also directed to a method of treating respiratory synctial virus syndrome in an individual in need of such treatment, comprising the step of administering to said individual an effective dose of the oligonucleotide of the present invention.

In therapeutic application, the oligonucleotides are utilized in a manner appropriate for treatment of a variety of conditions by inhibiting expression of the target genetic regions. For such therapy, the oligonucleotides alone or in combination can be formulated for a variety of modes of administration, including systemic, topical or localized administration. Techniques and formulations generally can be found in *Remington's Pharmaceutical Sciences,* Mack Publishing Co., Easton, Pa. The oligonucleotide active ingredient is generally combined with a pharamceutically accceptable carrier such as a diluent or excipient which can include fillers, extenders, binders, wetting agents, disintergrants, surface active agents or lubricants, depending on the nature of the mode of administration and dosage forms. Typical dosage forms include tablets, powders, liquid preparations including suspensions, emulsions, and solutions, granules, capsules and suppositories, as well as liquid preparations for injections, including liposome preparations.

For systemic administration, injection is preferred, including intramuscular, intravenous, intraperitoneal and subcutaneous. For injection, the oligonucleotides of the invention are formulated in liquid solutions, preferably in physiologically compatible buffers. In addition, the oligonucleotides can be formulated in solid form and redissolved or suspended immediately prior to use. Lyophilized forms are also incldued. Dosages that can be used for systemic administration preferably range from about 0.01 mg/kg to 50 mg/kg administered once or twice per day. However, different dosing schedules can be utilized depending on (1) the potency of an individual oligonucleotide at inhibiting the activity of its target DNA, (2) the severity or extent of the pathological disease state, or (3) the pharmacokinetic behavior of a given oligonucleotide.

The following examples are given for the purpose of illustrating various embodiments of the invention and are not meant to limit the present invention in any fashion.

EXAMPLE 1

Treatment of RSV-Infected Cells with Antisense Oligonucleotides Ex Vivo

Phosphorothioate derivatives of deoxyoligonucleotides antisense to the initiation region of NS2 and NS1 mRNAs were synthesized in an Applied Biosystems DNA synthesizer, followed by standard procedures of deprotection and then purification by gel-filtration chromatography using NAP-25 cartridges (Pharmacia). Stock solutions of 10 mM were made in sterile millipore-filtered water, and stored frozen until use.

HEp-2 cells were grown in monolayers in Eagle's minimal essential medium (1 x MEM) supplemented with fetal bovine serum (5%), L-glutamine, and penicillin and streptomycin. The cells, at a confluency of 60–80%, were infected with respiratory syncytial virus (Long strain) at an m.o.i. of 2; this was considered as 0 hours post-infection (p.i.). The media was replaced with fresh pre-warmed media at two time points: 4 hours and 30 hours p.i. Where used, the oligonucleotides were added to the medium at concentrations ranging from 5–20 mM at various times p.i, as indicated in the individual experiments. Whenever fresh medium was added to the cells, oligonucleotides were also added to maintain their concentration. At specified time after infection, the media supernatant was assayed for titer of released RS virions as described earlier on a lawn of HEp-2 cells. The cells were processed for, quantitation of viral macromolecules as described below.

EXAMPLE 2

Measurement of Viral RNA and Protein Synthesis

Viral mRNA synthesis in oligonucleotide-treated or untreated (control) cells was examined by first isolating the poly(A)$^+$ RNA from infected cells that were treated with actinomycin-D as described previously (Barik, 1992). To determine the relative amounts of the individual respiratory syncytial virus mRNAs, reverse transcription and PCR (RT-PCR) of poly(A)-selected viral mRNAs was then carried out using oligonucleotide primer pairs that are specific for each gene mRNA, essentially as described earlier (Mazumder et al., 1994). The Tm of all primer-RNA hybrids were around 45° C., so that the reverse transcription as well as the annealing step of PCR were carried out at 40° C. Following PCR, a portion of the reaction was analyzed in standard agarose gels, in the presence of ethidium bromide (1 μg/ml). The number of PCR cycles was chosen for each gene mRNA such that amplification was in the linear range.

To measure overall respiratory syncytial virus protein synthesis, infected cells at 18 hours p.i. were first treated with actinomycin D (2 μg/ml) for 2 hours in the presence of medium free of cysteine and methionine (Gibco-BRL). The medium was then removed and replaced with fresh cysteine- and methionine-free medium containing 0.5 mCi $^{35}$S-methionine and actinomycin D (2 mg/ml) per 5-cm diameter culture dish. Four hours later, the cells were washed with phosphate-buffered saline and lyzed and processed for immunoprecipitation as described before (Takacs et al., 1991). A mixture of monoclonal anti-RSV antibodies (Chemicon International, Temecula, Calif.) was used for immunoprecipitation. The precipitates were analyzed on SDS-PAGE followed by autoradiography of the gel. Western immunoblots of RSV-infected whole cell extracts were performed as described (Mazumder et al., 1994) using monoclonal antibodies against individual viral proteins.

EXAMPLE 3

Generation of Anitbodies against NS Proteins

The availability of large amounts of recombinant NS2 and NS1 enabled specific antisera to be raised against these proteins. Antisera were raised in rabbits by standard procedures (Mazumder et al., 1994) using polyacrylamide gel fragments containing the respective bacterial proteins as antigens. SDS-PAGE were carried out using 14% polyacrylamide gels according to Laemmli (1970), except for the analysis of NS proteins where a 20% polyacrylamide gel was used.

EXAMPLE 4

Cloning and Sequencing of RSV(long) NS Genes

The studies of the NS genes were performed using the Long strain of respiratory syncytial virus primarily because of familiarity with this strain and the availability of a reconstituted in vitro transcription system for this strain. While the nucleotide sequences of NS1 and NS2 genes were known for respiratory syncytial virus A2 strain (Collins and Wertz, 1985), those of respiratory syncytial virus Long, were not available.

Primers were designed against the non-coding regions of the NS1 and NS2 genes of the A2 strain and these primers were used to amplify the corresponding Long genes by reverse transcription and polymerase chain reaction (PCR). The genes were cloned in pGEM-4 and then sequenced. The results (TABLE 1) showed that the NS2 Long sequence had only 4 amino acid changes from A2, of which 2 were conservative: (A2 residue followed by Long) $Asn^4 \rightarrow Thr$; $Ile^{26} \rightarrow Thr$; $Lys^{38} \rightarrow Arg$; $Lys^{55} \rightarrow Arg$. NS1 sequences of the two strains differed by two amino acids both of which were conservative replacements (A2 followed by Long: $Val^{82} \rightarrow Ala$; $Leu^{105} \rightarrow Ile$). These results reiterated the high degree of sequence conservation between the Long and A2 strains. The authenticity of the sequences was further documented by the expression of recombinant NS proteins from these cloned genes.

TABLE 1

NS1 and NS2 sequence nonidentity between Long and A2 strains

| Nucleotide number | Codon (amino acid) Long | A2 |
|---|---|---|
| NS1: | | |
| 15 | TCG (Ser) | TCA (Ser) |
| 96 | GAC (Asp) | GAT (Asp) |
| 117 | AAT (Asn) | AAC (Asn) |
| 245, 246 | GCG (Ala) | GTA (Val) |
| 313 | ATA (Ile) | CTA (Leu) |
| NS2: | | |
| 11, 12 | ACC (Thr) | AAT (Asn) |
| 75 | ACT (Thr) | ACC (Thr) |
| 77 | ACA (Thr) | ATA (Ile) |
| 113 | AGA (Arg) | AAA (Lys) |
| 164 | AGA (Arg) | AAA (Lys) |
| 282 | CCG (Pro) | CCA (Pro) |

Nucleotide numbers, based on the coding region of the mRNA sequence, refer to altered nucleotides (underlined). Some changes (e.g, nucleotide 75 of NS2) are silent, i.e., produce a synonymous codon. RSV (Long) sequences are from this study; A2 sequences were taken from Collins and Wertz (1985).

Figure 1A:
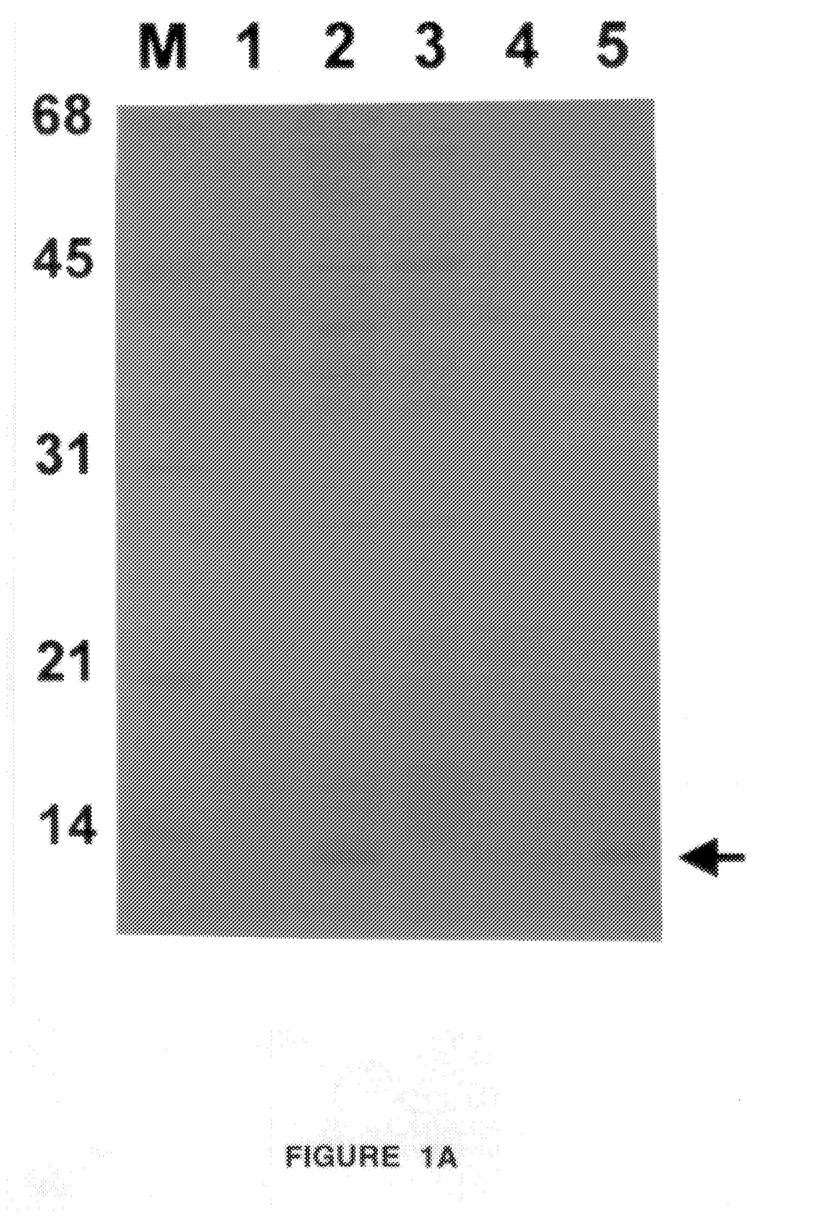
Figure 1B:
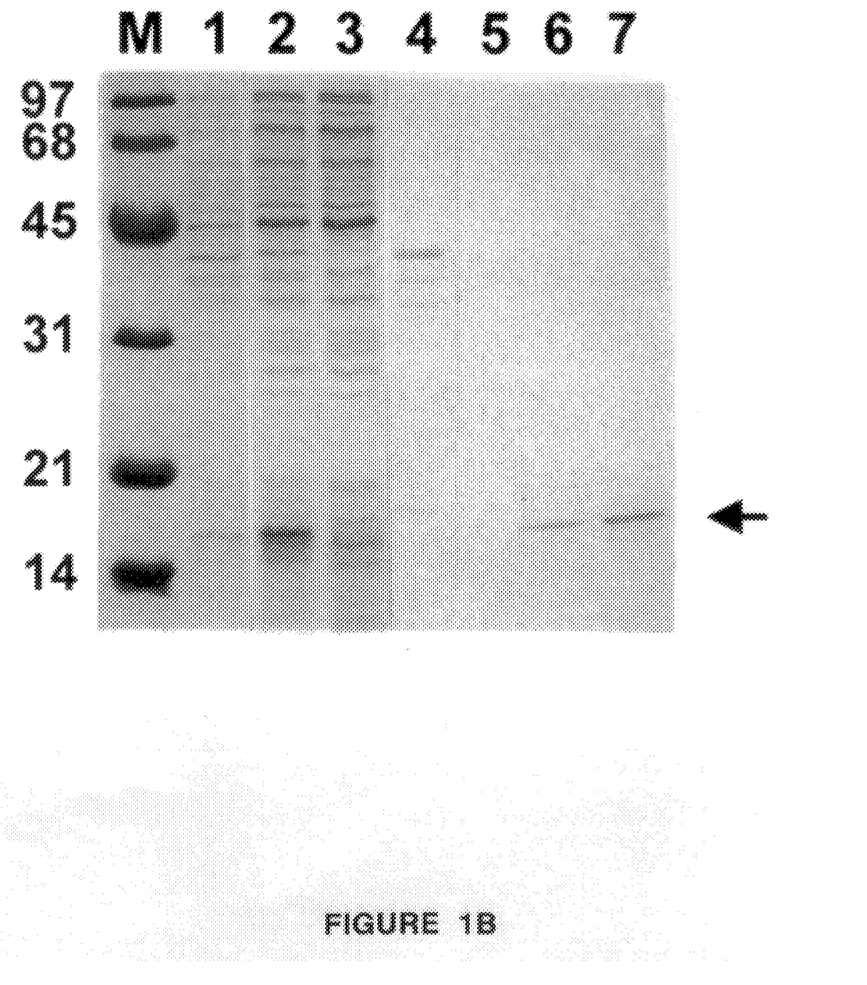

Once the protein coding sequence of the NS genes were known, the proteins were expressed recombinantly. To express the proteins in bacteria, a pair of primers were designed against the 5' and 3' termini of the Long coding sequences; these primers also contained NdeI and BamHI sites so that the products could be cloned into the same sites of the expression vector pET-3a (Mazumder et al., 1994). The final clones, confirmed by DNA sequencing, were introduced into E. coli BL21(DE3) which produces T7 RNA polymerase under the control of the lac promoter (Rosenberg et al., 1987). Upon induction with IPTG, transformants harboring pET-3a-NS2 and pET-3a-NS1 clones produced substantial amounts of the respective proteins, as shown in FIGS. 1A and B. In the gel conditions, NS2 and NS1 proteins migrated with $\sim M_r$ values of 16 k and 14 k, respectively, in close agreement with their predicted molecular weights.

The bacterially expressed NS2 and NS1 proteins were found to be insoluble; very little of either protein was found in the soluble cytosolic fraction (S100), the majority being present in the 100,000×g pellet, presumably as inclusion bodies (FIGS. 1A and 1B). While both proteins could be solubilized with 6M guanidinium hydrochloride (Gn-HCl), only the NS2 protein remained partly soluble after Gn-HCl was subsequently removed by dialysis (data not shown). The NS1 protein, on the other hand, completely precipitated out upon removal of Gn-HCl. The presence of 1M NaCl in the dialysis buffer could not prevent precipitation (data not shown).

Figure 2:
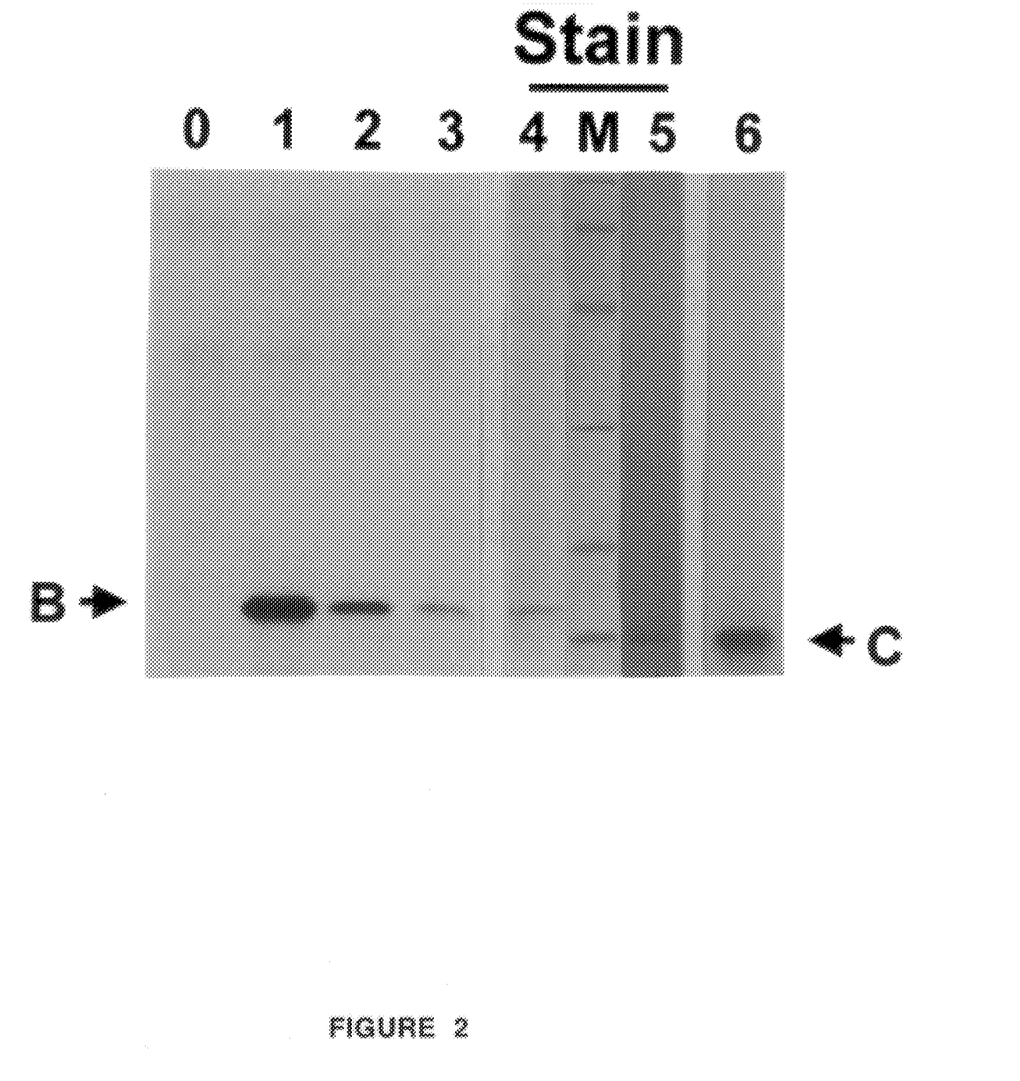

To further verify the authenticity of the recombinant proteins, the proteins were synthesized in cell-free translation systems in vitro. pGEM-4 and pET-3a clones of these genes were first linearized with appropriate restriction enzymes and the linearized templates were transcribed with T7 phage polymerase in vitro in the presence of the synthetic cap $^{7m}G^{(5')}ppp^{(5')}G$. This cap represents the natural 5'-cap structure of respiratory syncytial virus mRNAs (Barik, 1993). Translation of the in vitro synthesized NS2 and NS1 mRNAs in rabbit reticulocyte lysates was probably successful as judged by incorporation of $^{35}S$-methionine in trichloroacetic acid-precipitable material (data not shown). However, in SDS-PAGE analysis, labeled NS2 and NS1 polypeptides were difficult to visualize due to masking by a highly abundant endogenous reticulocyte protein (presumably globin) co-migrating in the same region of the gel. Therefore, the mRNAs were translated in wheat germ lysates; labeled proteins synthesized in this system were then compared with the bacterial proteins. Results of this comparison are presented in FIG. 2 which shows that proteins from both sources have identical mobilities in SDS-PAGE.

Figure 3:
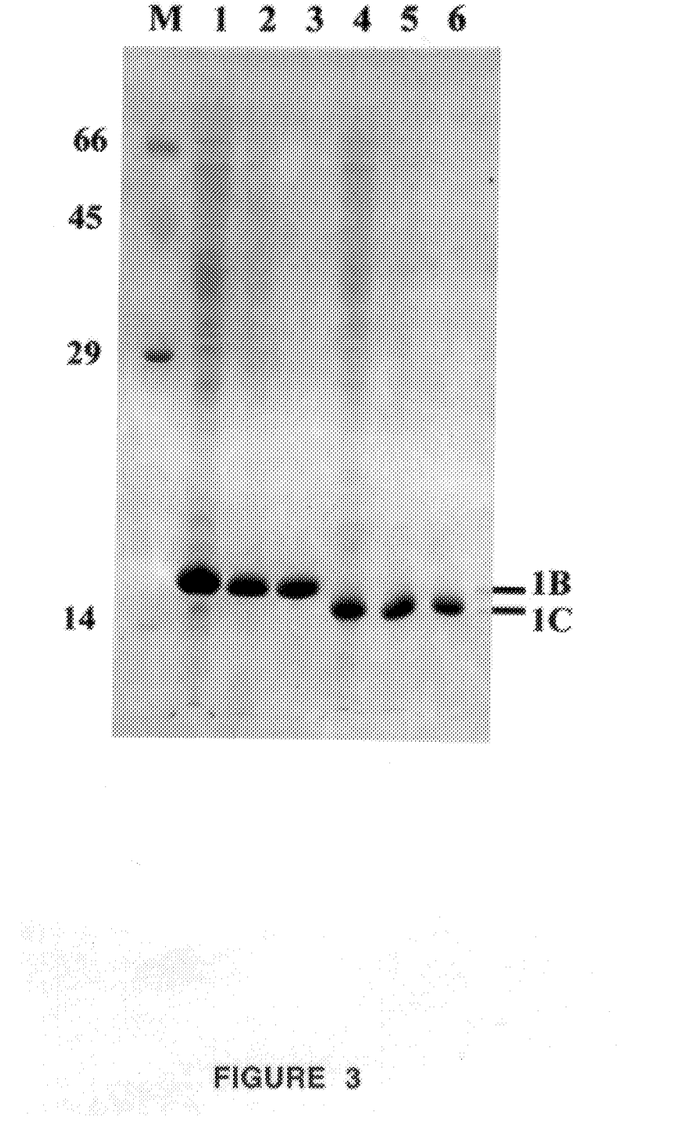

Since the bacterial proteins were insoluble, they were expressed in the baculovirus expression system, which generally produces large amounts of recombinant foreign proteins in soluble form. To this end, the genes were subcloned between the EcoRI and BglII sites of the baculovirus vector pVL1392, and generated recombinant baculoviruses using the BaculoGold expression system (Pharmingen, San Diego, Calif.). Sf21 cells were then infected with the recombinants and total proteins of the infected cells at 4 days p.i. were analyzed. Results presented in FIG. 3 show that both proteins were expressed in large quantities and more importantly, in soluble form. Starting with the S100 fraction containing the soluble proteins, both proteins were purified to greater than 90% homogeneity by gel filtration chromatography using Sephadex G-25 (FIG. 3, lanes 3, 6).

The availability of large amounts of recombinant NS2 and NS1 enabled specific antisera to be raised against these proteins. Antisera were raised in rabbits by standard procedures (Mazumder et al., 1994) using polyacrylamide gel fragments containing the respective bacterial proteins as antigens. In subsequent studies, these antibodies were used as reagents to study the NS proteins. Specific recognition of NS2 and NS1 proteins of RS-infected cells by antisera raised against bacterially expressed proteins further document the authenticity of the recombinant proteins. Previously, pulse labeling experiments showed that newly synthesized intracellular NS1 protein exhibited a Mr of ~14 k but appeared to be reduced by ~1.5 k upon subsequent chase (Huang et al., 1985), the half-life of the processing event being approximately 2 hours. Although no change of mobility was seen in these experiments, this could be due to a lower resolution of the two species in the electrophoretic conditions.

Figure 4:
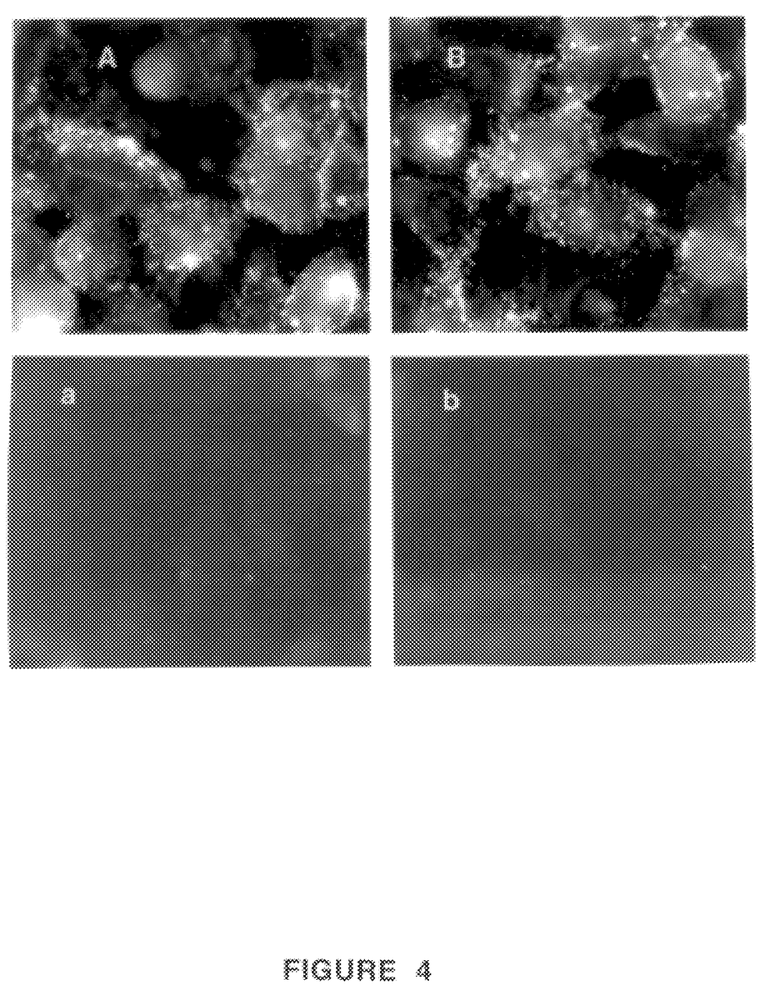

The anti-NS antibodies generated allowed the documentation of the synthesis of these proteins in respiratory syncytial virus infected cells and the determination of the intracellular localization of these proteins. With this objective, immunofluorescence studies of respiratory syncytial virus-infected HEp-2 cells were carried out at 24 hours p.i. Both proteins were found to be predominantly cytoplasmic in nature with a punctate distribution (FIG. 4). Neither protein could be detected in the nucleus or on the surface of non-permeabilized respiratory syncytial virus-infected cells, suggesting that both proteins are strictly intracellular and cytoplasmic. This was further confirmed by biochemical fractionation of the infected cells. Total extract of infected cells, prepared by sonication, was centrifuged at 100,000×g to pellet all particulate matter including unlysed cells, nuclei, and cellular organelles. The supernatants (S100), containing soluble cytosolic proteins, were subjected to western blot analysis using anti-NS2 and –NS1 antisera and the amounts of NS2 and NS1 were compared with those present in an equal volume of the unfractionated lysate. It was found that the majority (70–80%) of the NS2 and NS1 proteins of the infected cell were present in the soluble cytosol (data not shown).

EXAMPLE 5

Oligonucleotides Anti-Sense to NS1 and NS2 mRNAs Inhibit Respiratory Syncytial Virus Growth In order to generate phenotypic NS mutants of respiratory syncytial virus, a number of antisense oligonucleotides (or oligonucleotides) corresponding to both NS genes were designed. The most extensively studied ones are listed in TABLE 2 which include: oligonucleotides antisense to the translation initiation regions of their mRNAs (AS1 and AS2); two other oligonucleotides in the mRNA sense (S1, S2); and a random oligo with no significant similarity with any respiratory syncytial virus gene (R1). The oligonucleotides were added to infected (and control, uninfected) HEp-2 cells at various time points post-infection and the progression of infection was monitored by (a) determination of viral titer at 40 hours post-infection (p.i.); and (b) light microscopic observation of syncytia formation at various time points after infection up to 72 hours p.i.

Figure 5:
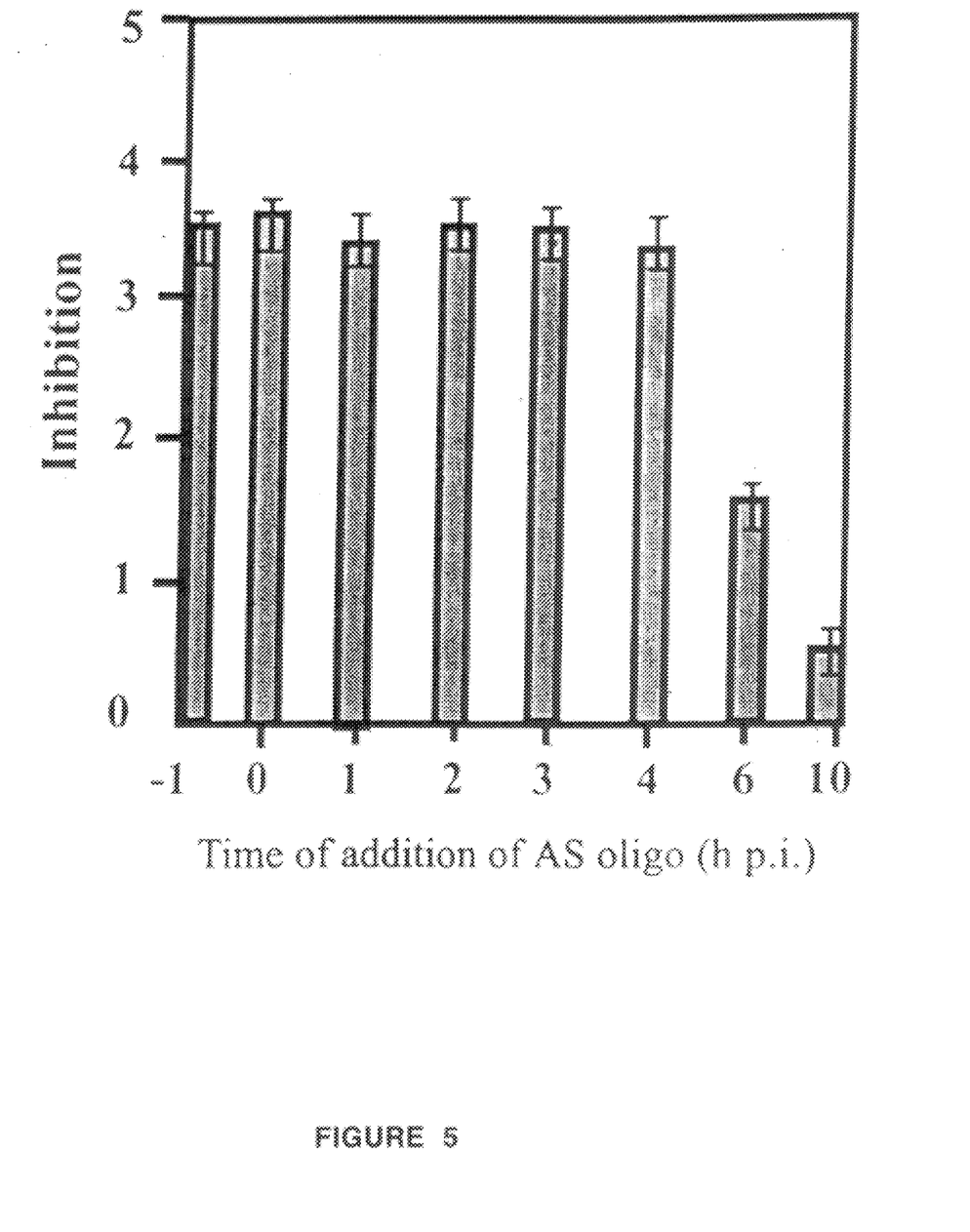
FIG. 5 shows the effect of addition of antisense -oligonucleotides at different stages of infection. The antisense oligonucleotides (15 mM final) were added to RSV-infected cells at indicated hours post-infection, and viral titer assayed 40 h p.i. as described below. The inhibition values are as in TABLE 2.

Results presented in TABLE 1 and FIG. 5 lead to the following major conclusions: (a) the antisense-oligonucleotides (AS1, AS2) strongly inhibit the yield of infectious respiratory syncytial virus; (b) the inhibition is most effective when the antisense-oligonucleotides were added within 5–6 hours of addition of the virus; (c) the sense oligonucleotides (S1, S2) or the random oligo (R1) had very little effect. Unless otherwise mentioned, oligonucleotides were added at 2 hours p.i.

In order to determine whether the inhibitory effect of the antisense-oligonucleotides was specific on respiratory syncytial virus, their effect was tested on three other viruses, viz., the bovine and ovine strains of respiratory syncytial virus and vesicular stomatitis virus (VSV). The bovine and ovine strains of respiratory syncytial virus are highly similar to the human respiratory syncytial virus; however, the sequences of their NS genes differ from that of respiratory syncytial virus NS genes in the region against which the antisense-oligonucleotides were designed. VSV is a member of the Rhabdoviridae family and its RNA genome has no detectable sequence homology with that of respiratory syncytial virus. As also shown in TABLE 1, none of these viruses are affected by the AS1 and AS2 oligonucleotides. The reason for a modest effect of the R2 oligo on human respiratory syncytial virus titer is not clear, but could be due to limited homology with an unidentified respiratory syncytial virus sequence. No inhibitory effect was discernible by monitoring the syncytia formation. Taken together, these results demonstrate a specific inhibitory effect of the AS1 and AS2 oligonucleotides on respiratory syncytial virus growth in cell culture.

EXAMPLE 6

Figure 6:
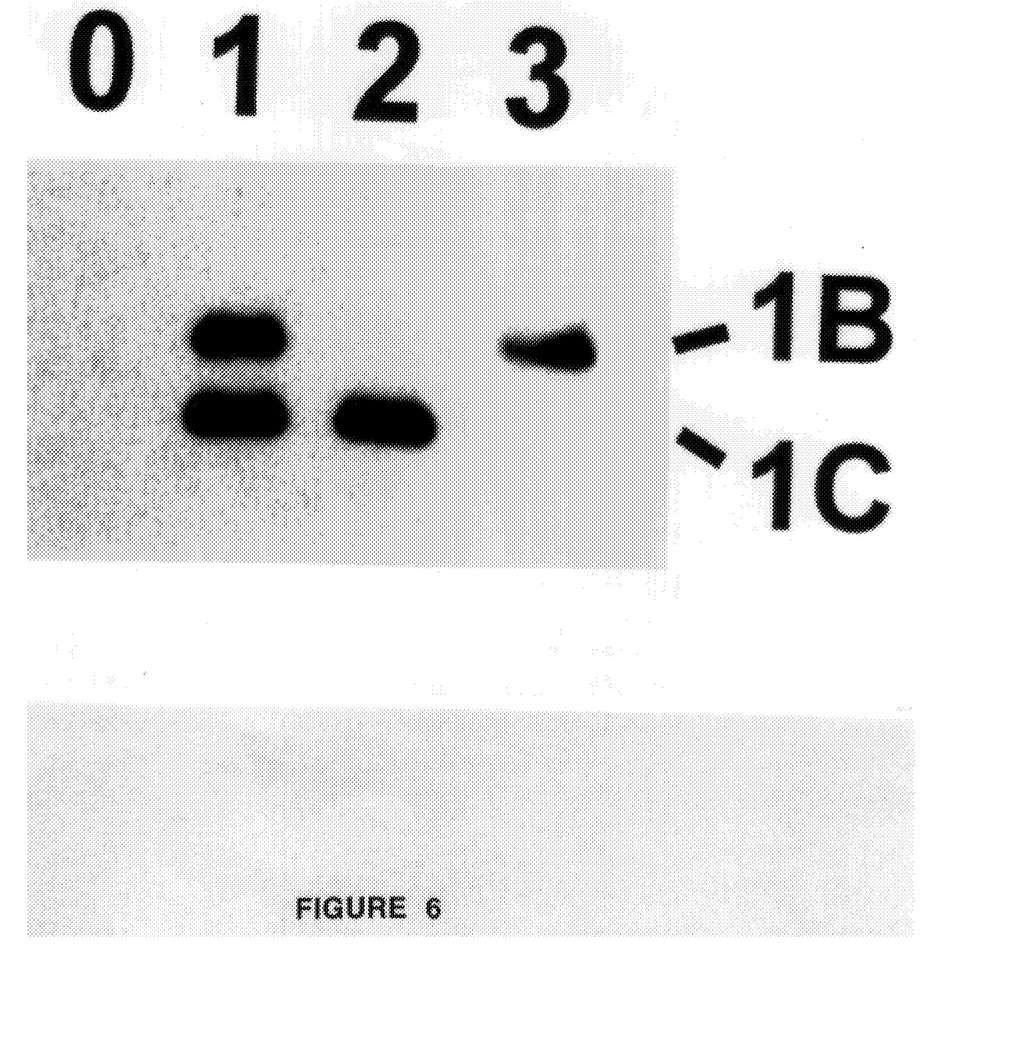

Anti-NS Oligonucleotides Specifically Inhibit the Synthesis of Respiratory Syncytial Virus NS Proteins To elucidate the mechanism of action of the antisense oligonucleotides, whether they inhibit the synthesis of the corresponding NS proteins was examined. Extracts of antisense-treated respiratory syncytial virus-infected HEp-2 cells were subjected to immunoblot (Western Blot) analysis using antibodies against either NS1 or NS2 proteins. Results presented in FIG. 6 clearly show a near-complete loss of each specific NS protein in the presence of the corresponding anti-sense oligo, suggesting that the oligonucleotides inhibited the synthesis of the NS proteins and this effect was highly specific for the individual NS proteins.

Whether the antisense oligonucleotides inhibited the synthesis of any other viral proteins was then investigated. This was achieved through two different techniques. In the first, $^{35}$S-labeled respiratory syncytial virus proteins were immunoprecipitated from oligonucleotide-treated (or, control untreated) using a mixed respiratory syncytial virus-antibody. Analysis of these proteins did not reveal any significant difference between oligonucleotide-treated and untreated cells (FIG. 7), suggesting that the antisense oligonucleotides have little effect, if any, on general respiratory syncytial virus protein synthesis.

Figure 8:
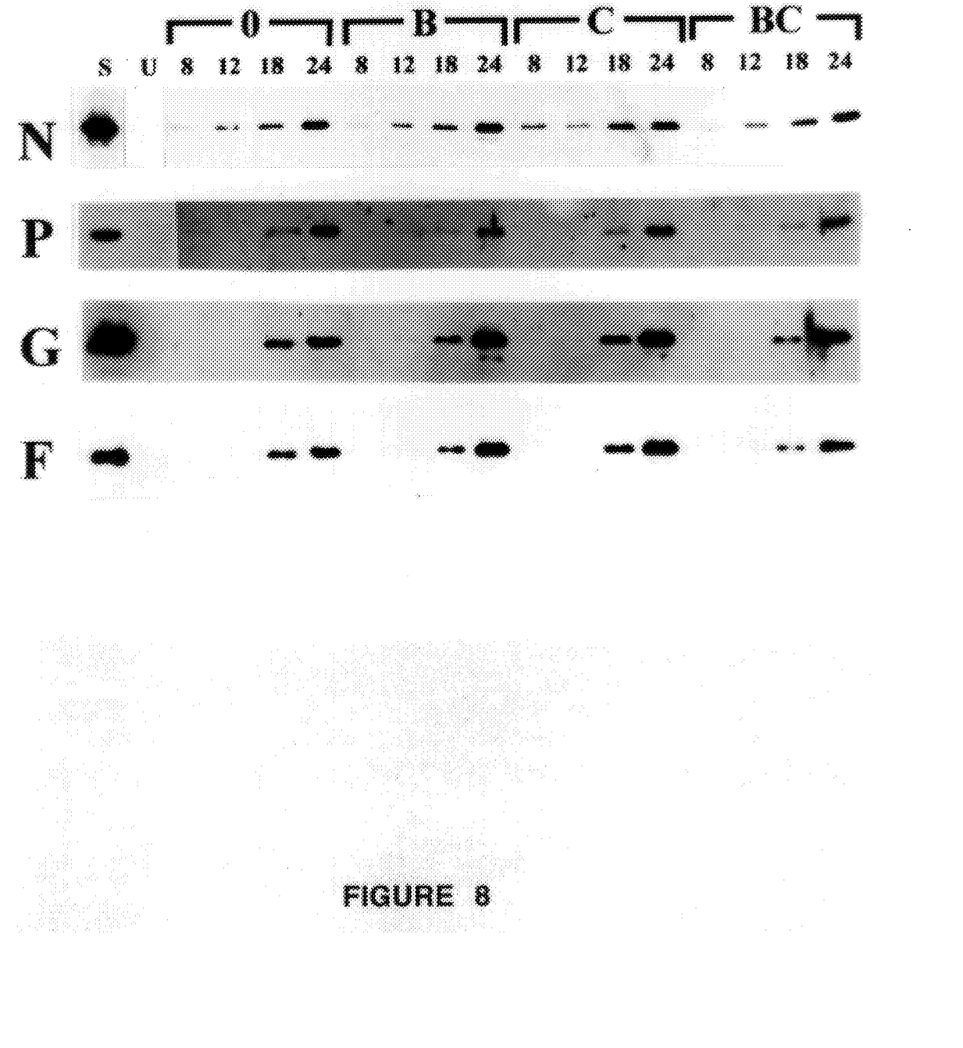
FIG. 8 shows the immunoblot analysis of individual respiratory syncytial virus proteins. Western analysis was performed as described below. The various respiratory syncytial virus proteins (N, P, G, F) are indicated. Infected cells were indicated at the indicated times p.i. Panels 0=untreated (no oligo); B=AS2-treated; C=AS1-treated; BC=AS1 and AS2-treated. U=uninfected control. S=mature RS virion.

Since the molecular weights and quantities of different respiratory syncytial virus proteins have a wide margin, they are difficult to identify in a single SDS-PAGE analysis. Thus, in order to identify each viral protein, the treated and untreated cell extracts were subjected to Western Blot analysis using protein-specific monoclonal or monospecific antibodies. Results of these studies (FIG. 8) also failed to reveal any effect of the oligonucleotides on respiratory syncytial virus protein synthesis.

EXAMPLE 7

Figure 9:
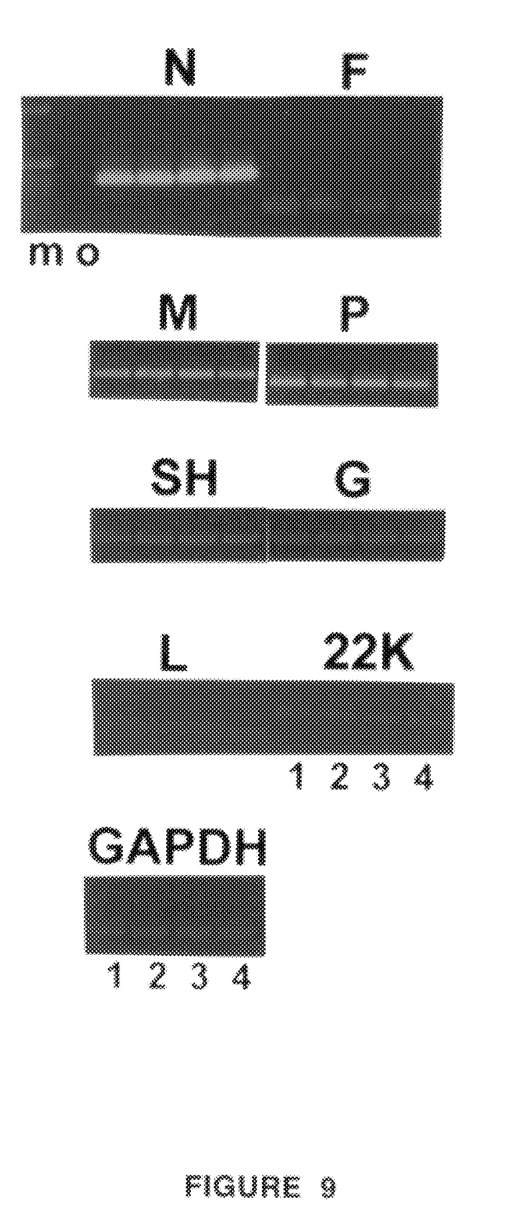
FIG. 9 shows the quantitation of respiratory syncytial virus mRNA in oligo-treated cells. RT-PCR detection of individual respiratory syncytial virus mRNAs were carried out as described below. The various genes (N, F etc.) are indicated. The number of cycles of PCR were as follows: N, 20; P, 20; M, 20; SH, 20; G, 22; F, 24; 22K, 25; L, 30 cycles. An ethidium bromide-stained gel of each PCR product is shown. m=marker; 0=uninfected cell mRNA, amplified with N primers.

Anti-NS Oligonucleotides do not Inhibit Respiratory Syncytial Virus Transcription or Replication Ex Vivo To further define the anti-viral effect of the antisense oligonucleotides, whether they had any effect on viral mRNA, full-length viral genomic RNA, and other (non-NS) viral proteins was investigated. The mRNA levels were detected by RT-PCR using specific primers. The linearity of the PCR was ascertained by (a) performing amplification over various number of cycles; and (b) the fact that the quantities of the final PCR product from a given mRNA was roughly proportional to its molar amount in respiratory syncytial virus-infected cells, based on polarity of transcription (Barik, 1992). As shown in FIG. 9, the antisense oligonucleotides had no significant effect on the steady state level of all respiratory syncytial virus mRNAs tested.

Since the major boost of respiratory syncytial virus translation and transcription occurs from the replication of the viral genome and the resultant secondary transcription of the replicated genomes, and since there was no effect of the antisense oligonucleotides on global respiratory syncytial virus protein or mRNA synthesis (FIGS. 7, 8, 9), it is reasonable to conclude the oligonucleotides had little effect on replication. Nevertheless, this conclusion was further confirmed through RT-PCR quantitation of full-length negative strand genomic RNA using primers corresponding to genes that are separated in distance on the genome, viz., one primer for gene N, and the other for gene M, which are separated by gene P. The results of such analysis directly showed that the antisense oilgonucleotides had no effect on respiratory syncytial virus genome replication (data not shown).

EXAMPLE 8

NS Proteins Interact with Respiratory Syncytial Virus Nucleocapsid

Figure 7:
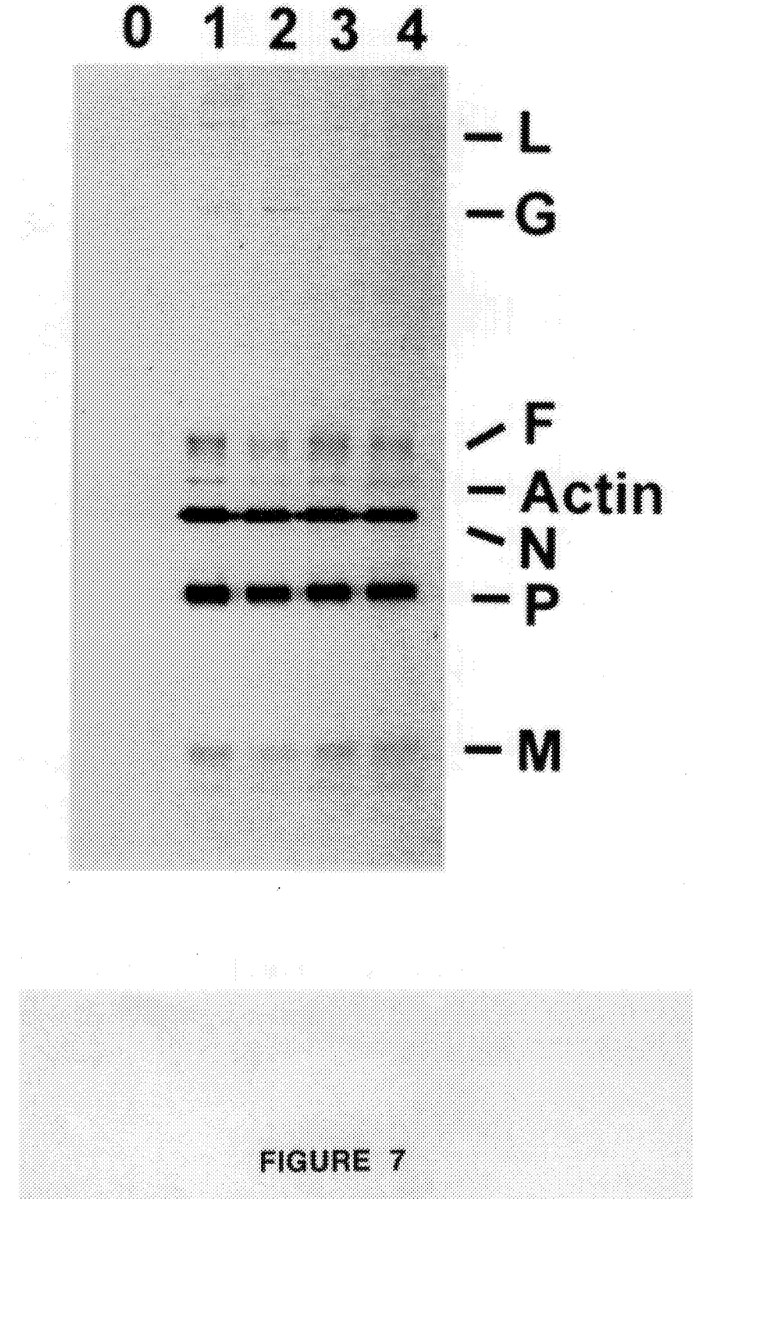
FIG. 7 shows the lack of effect of antisense oligonucleotides on respiratory syncytial virus protein synthesis. $^{35}$S-Met-labeled respiratory syncytial virus proteins were immunoprecipitated from antisense-treated or untreated cells as described below. An autoradiograph of the SDS-PAGE gel is shown.

As mentioned earlier, the function(s) of respiratory syncytial virus NS proteins remain unknown. To understand their role, studies of the affinity of these proteins for the viral nucleocapsid were carried out. Using ionic conditions very similar to respiratory syncytial virus transcription buffer (Barik, 1992a; Mazumder and Barik, 1994), both proteins bound to the nucleocapsid in a concentration-dependent manner (FIG. 7). At saturating concentrations, about 50–60 ng NS2/NS1 bind to ~250 ng nucleocapsid.

The present invention discloses the: (a) sequencing of the NS genes of the respiratory syncytial virus Long strain; (b) expression of both NS proteins in recombinant form; (c) production of anti-NS antibodies; (c) designing of anti-sense oligonucleotides that specifically inhibit the expression of NS proteins and inhibits respiratory syncytial virus growth in cell culture; (d) demonstration of an essential role NS proteins in respiratory syncytial virus growth; and (e) demonstration that the NS proteins are not required for transcription and replication of the virus.

A corollary of the conclusions stated above is that NS proteins are actually required in a post-replicative step, although the fact that viral growth becomes refractory to the effect of antisense oligonucleotides after about 6 hours of infection suggest that the NS protein may be able to at least initiate their function relatively early in infection. This is in agreement with the fact the NS proteins can be detected very early in infection, within about 2 hours (data not shown). Furthermore, since antisense oligonucleotides against NS1 and NS2 had similar effects in all these studies, they may be involved in similar, if not identical, roles in viral growth cycle, and perhaps work together. One possibility is that they have a role in viral morphogenesis.

The efficacy of the antisense oligonucleotides in inhibiting respiratory syncytial virus growth holds enormous promise in the management of respiratory syncytial virus infection and pathogenesis for a number of reasons. As alluded to earlier, a reliable respiratory syncytial virus vaccine is yet to materialize. At the same time, it is being increasingly clear that a natural respiratory syncytial virus infection may provoke proper immune response to generate a Th1 type response beneficial to the host, whereas use of denatured (formalin- or heat-inactivated) virus as vaccine may produce untoward side effects, known as "immunopotentiation", resulting from a Th2 response (Graham et al., 1991; Seder and Paul, 1994). Thus, the fact the antisense oligonucleotides do not prevent the primary round of infection but rather limit the infection in the small number of initially infected cells may in fact be beneficial to the host, since this will generate a proper and natural anti-respiratory syncytial virus immune response in the host to prevent further infection. Thus, in essence, the antisense oligonucleotides should act as vaccines without having the side-effects of conventional vaccines. No detectable cytopathic effect in cell culture has been detected, using a variety of cell lines, including cells of epithelial, monocytic, and fibroblast origin. If some toxicity is found, it should be possible to reduce it by lowering the concentration of the AS oligonucleotides.

The delivery of the antisense oligonucleotides to the animal host should, at least in principle be particularly easy, in contrast to conventional vaccines. They can, for example, be delivered as an aerosol directly into the nose or in the lower respiratory tract, either alone or in combination with other antiviral medications. This will not only deliver the antisense oligonucleotides directly at the site of respiratory syncytial virus infection, but also aid in maintaining a higher local concentration of the oligonucleotides, thus minimizing systemic toxicity. The relative stability of the oligonucleotides, especially when supplied as dried powder that can be reconstituted with sterile water, makes them ideal drugs for global use, such as in remote areas and countries, in field trials, and in outdoors in general.

Lastly, the availability of soluble recombinant NS proteins and their antibodies provide an opportunity to study the properties of these proteins in vitro as well as ex vivo. Large quantities of NS2 and NS1 proteins may also be useful for X-ray crystallographic studies of these unique nonstructural proteins. The detection of these proteins early in the viral life cycle is consistent with the genome-3'-end location of their genes. It is intriguing that both proteins bind to purified viral nucleocapsid in vitro and yet are not found in the mature virus. While it remains to be seen whether they also associate in vivo with the nucleocapsid or any of its constituents, it is possible that they are excluded or displaced only during the final stages of morphogenesis or packaging of the virion. Anti-NS2/NS1 antibodies described here are useful tools to study such interactions.

TABLE 2

Specific inhibition of human RSV by anti-NS oilgos

| Oligo name | Oligo sequence (5' to 3') | Virus tested in viral titer | Reduction at 40 h p.i. | Syn-cytiur |
|---|---|---|---|---|
| AS1 | CAATGAATTGCTGCCCATC | HRSV | 3.3; 3.5 | − |
|  |  | BRSV | 0.02; 0.03 | + |
|  |  | ORSV | 0.01; 0.02 | + |
|  |  | VSV | 0.01; 0.01 | CPE |
| AS2 | TTGTGGGTTGTGTCCATG | HRSV | 3.2; 3.1 | − |
|  |  | BRSV | 0.03; 0.03 | + |
|  |  | ORSV | 0.01; 0.004 | + |
|  |  | VSV | 0.01; 0.005 | CPE |
| S1 | GATGGGCAGCAATTCATTG | HRSV | 0.09; 0.12 | + |
| S2 | CATGGACACAACCCACAA | HRSV | 0.04; 0.07 | + |
| R1 | ACGTACGTACGTACGTAC | HRSV | 0.01; 0.03 | + |
| R2 | AAGGCCTTAAGGCCTTAA | HRSV | 0.3; 0.22 | + |

Synthesis and use of the oligonucleotides have been described above. In this experiment, oligonucleotides were used at a final concentration of 20 mM and added at 2 hours p.i. The AS and S oligonucleotides were all designed against the human respiratory syncytial virus gene sequences and are complementary to each other (i.e., AS1 to S1, and AS2 to S2). The letters in front of respiratory syncytial virus indicate the species: H=human; B=bovine; O=ovine. Index of reduction in viral titer (at 40 hours p.i.) is expressed as $-\log_{10}$ (titer in oligo-treated/titer in untreated culture). Example: if the titer of the treated culture is 1000 times lower than that of the untreated control, the index is=−log (1/1000)=3.0. Syncytia were scored at 72 hours p.i. (+ indicates extensive syncytia characteristic of respiratory syncytial virus; − indicates no detectable syncytia). Unlike respiratory syncytial virus, VSV does not produce syncytia, but gives rise to the characteristic cytopathic effect (CPE) evidenced by the rounding and detachment of cells of the monolayer. Results using HEp-2 cells are shown here, although use of A549 cells produced essentially identical results.

The following references were cited herein:

Barik, S. (1992). Transcription of human respiratory syncytial virus genome RNA in vitro: requirement of cellular factor(s). J. Virol. 66, 6813–6818.

Barik, S. (1993). The structure of the 5' terminal cap of the respiratory syncytial virus mRNA. J. Gen. Virol. 74, 485–490.

Collins, P. L. (1991). The molecular biology of human respiratory syncytial virus (RSV) of the genus *Pneumovirus*, p. 103–162. In D. W. Kingsbury (ed.), The Paramyxoviruses. Plenum Publishing Co., New York.

Collins, P. L., and Wertz, G. W. (1985). Nucleotide sequences of the NS2 and NS1 nonstructural protein mRNAs of human respiratory syncytial virus. Virology 143, 442–451.

Elango, N., M. Satake, and Venkatesan, S. (1985). mRNA sequence of three respiratory syncytial virus genes encoding two nonstructural proteins and a 22K structural protein. J. Virol. 55, 101–110.

Graham, B. S., Henderson, G. S., Tang, Y.-W., Lu, X., Neuzil, K. M., and Colley, D. G. (1993). Priming immunization determines cytokine mRNA expression patterns in lungs of mice challenged with respiratory syncytial virus. J. Immunol. 151, 2032–2040.

Hall, C. B. (1994). Prospects for a respiratory syncytial virus vaccine. Science 265, 1393–1394.

Heilman, C. A. (1990). From the National Institute of Allergy and Infectious Diseases and the World Health Organisation: Respiratory syncytial and parainfluenza viruses. J. Infect. Dis. 161, 402–406.

Huang, Y. T., Collins, P. L. and Wertz, G. W. (1985) Characterization of the ten proteins of human respiratory syncytial virus: Identification of a fourth envelope associated protein. Virus Res. 2, 157–173.

Johnson, P. R. and Collins, P. L. (1989) The 1B (NS2), 1C (NS1) and N proteins of human respiratory syncytial virus (RSV) of antigenic subgroups A and B: sequence conservation and divergence within RSV genomic DNA. J. Gen. Virol. 70, 1539–1547.

Laemmli, U. K. (1970) Cleavage of structural proteins during the assembly of the head of bacteriophage T4. Nature (London) 227, 680–685.

Mazumder, B., Adhikary, G. and Barik, S. (1994) Bacterial expression of human respiratory syncytial virus phosphoprotein P and identification of $Ser^{237}$ as the site of phosphorylation by cellular casein kinase II. Virology 205, 93–103.

Mazumder, B. and Barik, S. (1994) Requirement of casein kinase II-mediated phosphorylation for the transcriptional activity of human respiratory syncytial virus phosphoprotein P: transdominant negative phenotype of phosphorylation-defective P mutants. Virology 205, 104–111.

Rosenberg, A. H., Lade, B. N., Chui, D., Lin, S.-W., Dunn, J. J. and Studier, F. W. (1987) Vectors for selective expression of cloned DNAs by T7 RNA polymerase. Gene 56, 125–135.

Seder, R. A., and Paul, W. E. (1994). Acquisition of lymphokine-producing phenotype by $CD4^+$ T cells. Annu. Rev. Immunol. 12, 635–673.

Takacs, A. M., Perrine, K. G., Barik, S., and Banerjee, A. K. (1991). Alteration of specific amino acid residues in the acidic domain of VSV phosphoprotein (P) converts a GAL4-P(I) hybrid into a transcriptional activator. New Biol. 3, 581–591.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An oligonucleotide having the sequence complementary to a respiratory syncytial virus nucleotide sequence selected from the group consisting of nucleotide number 98-116 (SEQ ID No. 1) of the respiratory syncytial virus antigenome or nucleotide sequence number 627-645 (SEQ ID No. 2) of the respiratory syncytial virus antigenome.

2. A composition comprising the oligonucleotide according to claim 1 and a physiologically acceptable carrier therefore.

3. An oligonucleotide having the nucleotide sequence: CAATGAATTGCTGCCCATC (SEQ ID No. 1).

4. A composition comprising the oligonucleotide according to claim 3 and a physiologically acceptable carrier therefore.

5. An oligonucleotide having the nucleotide sequence: TTGTGGGTTGTGTCCATG (SEQ ID No. 2).

6. A composition comprising the oligonucleotide according to claim 5 and a physiologically acceptable carrier therefore.

* * * * *

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 19 base pairs
        ( B ) TYPE: nucleic acid
        ( C ) STRANDEDNESS: double- stranded
        ( D ) TOPOLOGY: linear     ( i i ) MOLECULE TYPE: DNA     ( i i i ) HYPOTHETICAL: no     ( i v ) ANTI-SENSE: Yes ( v ) SEQUENCE DESCRIPTION: SEQ ID NO:1:

CAATGAATTG CTGCCCATC 19

( 2 ) INFORMATION FOR SEQ ID NO: 2:

( i ) SEQUENCE CHARACTERISTICS:
        ( A ) LENGTH: 18 base pairs
        ( B ) TYPE: nucleic acid
        ( C ) STRANDEDNESS: double- stranded
        ( D ) TOPOLOGY: linear     ( i i ) MOLECULE TYPE: DNA     ( i i i ) HYPOTHETICAL: no     ( i v ) ANTI-SENSE: Yes     ( v ) SEQUENCE DESCRIPTION: SEQ ID NO:2:

TTGTGGGTTG TGTCCATG 18

( 2 ) INFORMATION FOR SEQ ID NO: 3:

( i ) SEQUENCE CHARACTERISTICS:
        ( A ) LENGTH: 19 base pairs
        ( B ) TYPE: nucleic acid
        ( C ) STRANDEDNESS: double- stranded
        ( D ) TOPOLOGY: linear     ( i i ) MOLECULE TYPE: DNA     ( i i i ) HYPOTHETICAL: no     ( i v ) ANTI-SENSE: No     ( v ) SEQUENCE DESCRIPTION: SEQ ID NO:3:

GATGGGCAGC AATTCATTG 19

( 2 ) INFORMATION FOR SEQ ID NO: 4:

( i ) SEQUENCE CHARACTERISTICS:
        ( A ) LENGTH: 18 base pairs
        ( B ) TYPE: nucleic acid
        ( C ) STRANDEDNESS: double- stranded
        ( D ) TOPOLOGY: linear     ( i i ) MOLECULE TYPE: DNA     ( i i i ) HYPOTHETICAL: no     ( i v ) ANTI-SENSE: No     ( v ) SEQUENCE DESCRIPTION: SEQ ID NO:4:

CATGGACACA ACCCACAA 18

( 2 ) INFORMATION FOR SEQ ID NO: 5:

( i ) SEQUENCE CHARACTERISTICS:
        ( A ) LENGTH: 18 base pairs
        ( B ) TYPE: nucleic acid
        ( C ) STRANDEDNESS: double- stranded
        ( D ) TOPOLOGY: linear     ( i i ) MOLECULE TYPE: DNA     ( i i i ) HYPOTHETICAL: no     ( i v ) ANTI-SENSE: No     ( v ) SEQUENCE DESCRIPTION: SEQ ID NO:5:

ACGTACGTAC GTACGTAC 18

(2) INFORMATION FOR SEQ ID NO: 6:

(i) SEQUENCE CHARACTERISTICS:
        (A) LENGTH: 18 base pairs
        (B) TYPE: nucleic acid
        (C) STRANDEDNESS: double-stranded
        (D) TOPOLOGY: linear     (ii) MOLECULE TYPE: DNA     (iii) HYPOTHETICAL: no     (iv) ANTI-SENSE: No     (v) SEQUENCE DESCRIPTION: SEQ ID NO:6:

AAGGCCTTAA GGCCTTAA        18